(12) United States Patent
Hopka et al.

(10) Patent No.: US 10,309,944 B2
(45) Date of Patent: Jun. 4, 2019

(54) ELECTROSTATIC PM SENSOR ELECTRODE DIAGNOSTICS

(71) Applicant: Ford Global Technologies, LLC, Dearborn, MI (US)

(72) Inventors: Michael Brendan Hopka, Milford, MI (US); David John Kubinski, Canton, MI (US); David Bilby, Auburn Hills, MI (US); Michiel J. Van Nieuwstadt, Ann Arbor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 123 days.

(21) Appl. No.: 15/256,890

(22) Filed: Sep. 6, 2016

(65) Prior Publication Data

US 2018/0067090 A1 Mar. 8, 2018

(51) Int. Cl.
*G01N 33/00* (2006.01)
*F01N 13/00* (2010.01)
*F01N 11/00* (2006.01)

(52) U.S. Cl.
CPC .......... *G01N 33/007* (2013.01); *F01N 11/00* (2013.01); *F01N 13/008* (2013.01); *G01N 33/0036* (2013.01); *F01N 2550/04* (2013.01); *F01N 2560/05* (2013.01); *Y02A 50/25* (2018.01); *Y02T 10/47* (2013.01)

(58) Field of Classification Search
CPC .. G01N 33/007; G01N 33/0036; F01N 11/00; F01N 13/008
See application file for complete search history.

(56) References Cited

U.S. PATENT DOCUMENTS

| 6,397,662 B1* | 6/2002 | Alkhoury | E06B 3/5409 73/31.04 |
| 8,707,761 B2* | 4/2014 | Maeda | G01N 15/0656 73/23.33 |
| 8,823,401 B2 | 9/2014 | Roth et al. | |
| 9,188,034 B2 | 11/2015 | Hopka et al. | |
| 2008/0024111 A1 | 1/2008 | Dorfmueller et al. | |
| 2011/0015824 A1 | 1/2011 | Ante et al. | |

(Continued)

FOREIGN PATENT DOCUMENTS

| JP | 4574411 B2 | 11/2010 |
| JP | 2014055820 A | 3/2014 |

*Primary Examiner* — David Z Huang
(74) *Attorney, Agent, or Firm* — Ray Coppiellie; Brooks Kushman P.C.

(57) ABSTRACT

Particulate matter (PM) sensors and diagnostics performed using the PM sensors are disclosed. The PM sensors and diagnostics may be used in exhaust systems, such as vehicle exhaust systems, to detect soot. In at least one embodiment, an electrostatic particulate matter (PM) sensor is provided including first and second spaced apart electrodes forming a bulk gap therebetween having a bulk distance and a localized gap therebetween having a localized distance less than the bulk distance. A controller may be configured to control a voltage between the electrodes to induce an electrostatic discharge at the localized gap at a lower voltage than at the bulk gap. Various diagnostics may be performed using the disclosed PM sensors, including a wiring/continuity diagnostic, a soot detection plausibility diagnostic, and/or an installation diagnostic.

12 Claims, 5 Drawing Sheets

(56) References Cited

U.S. PATENT DOCUMENTS

| | | |
|---|---|---|
| 2011/0088450 A1 | 4/2011 | Ante et al. |
| 2012/0125081 A1 | 5/2012 | Yadav et al. |
| 2012/0312074 A1 | 12/2012 | Allmendinger et al. |
| 2013/0318948 A1 | 12/2013 | Van Marion |
| 2015/0168285 A1 | 6/2015 | Hedayat et al. |
| 2015/0211429 A1 | 7/2015 | Hocken et al. |
| 2016/0160721 A1 | 6/2016 | Zhang |
| 2017/0130636 A1* | 5/2017 | Bilby ................. F01N 3/023 |
| 2017/0155373 A1* | 6/2017 | Ruby ................. H03H 9/25 |

* cited by examiner

ELECTROSTATIC PM SENSOR ELECTRODE DIAGNOSTICS

TECHNICAL FIELD

The present disclosure relates to electrostatic particulate matter (PM) sensor electrode diagnostics, for example, for use in vehicle exhaust systems.

BACKGROUND

Diesel vehicles, and some gasoline fueled vehicles, generally include an exhaust particulate filter to reduce emissions of solid particles that are products of fuel combustion. Some regulations, such as US EPA and California Air Resources Board (CARB), require that these filters be diagnosed for leaks. One solution to this diagnostics problem is an electrostatic particulate matter (PM) sensor that detects the amount of soot and other solid particles in vehicle exhaust. This sensor generally relies on a pair of parallel electrodes separated by an air gap with a voltage across the electrodes to detect particulate matter (PM). Because the soot that enters the sensor with exhaust gas is usually charged (for example, about 33% positive charge and 33% negative charge), a portion of the soot will typically deposit on the sensor electrodes. As more particles accumulate on each electrode, they may form dendritic structures perpendicular to the electrode surface. Charge tends to pool at the tip of the dendrites as they grow and, eventually, they may become long enough that the electrostatic force attracting the particles to the opposing electrode exceeds the force holding the dendrite together and to the electrode wall. Once the force holding the dendrite is exceeded, it may break off and carry its pooled charge to the opposite electrode. This charge transfer may be measured as a current between the electrodes. The rate at which break-off and charge transfer occurs may be roughly proportional to the rate at which soot is entering the sensor.

SUMMARY

In at least one embodiment, an electrostatic particulate matter (PM) sensor is provided. The PM sensor may include first and second spaced apart electrodes forming a bulk gap therebetween having a bulk distance and a localized gap therebetween having a localized distance less than the bulk distance; and a controller configured to control a voltage between the electrodes to induce an electrostatic discharge at the localized gap at a lower voltage than at the bulk gap.

In one embodiment, the localized gap is formed by a protrusion extending from one of the first or second electrodes towards the other. In another embodiment, the localized gap is formed by a protrusion extending from each of the first and second electrodes towards the other. The protrusion may be integrally formed with the electrode from which it extends or the protrusion may comprise a different material than the electrode from which it extends. The localized distance may be at least 5% or at least 25% smaller than the bulk distance. In one embodiment, the localized gap is located within 10% of a distal end of the electrodes.

In at least one embodiment, an electrostatic particulate matter (PM) sensor is provided. The PM sensor may include first and second spaced apart electrodes forming a bulk gap therebetween having a bulk distance and a localized gap therebetween having a localized distance less than the bulk distance; and a controller configured to maintain a voltage between the electrodes that is constant during a first operating state.

In one embodiment, the controller may be configured to increase the voltage between the first and second electrodes during a second operating state to induce an electrostatic discharge at the localized gap if there are no electrical faults in the PM sensor. The controller may be configured to increase the voltage between the electrodes to at least 50% above the constant voltage of the first operating state.

In another embodiment, during a third operating state, the controller may be configured to incrementally increase the voltage between the first and second electrodes above the constant voltage of the first operating state until a current detected between the electrodes is greater than a discharge threshold current. A breakdown voltage at which the current is detected may be compared to a calculated breakdown voltage of an exhaust gas passing through the PM sensor at the localized gap, and, if the breakdown voltage is greater than the calculated breakdown voltage an installation fault flag may generated. The controller may be configured to perform the steps of incrementally increasing the voltage and comparing a breakdown voltage to a calculated breakdown voltage multiple times at different exhaust gas temperatures, and, if the breakdown voltage is greater than the calculated breakdown voltage at least a threshold number of times of the multiple times, an installation fault flag may be generated. The controller may be configured to incrementally increase the voltage continuously or in a step-wise manner.

In at least one embodiment, an electrostatic particulate matter (PM) sensor is provided. The PM sensor may include first and second spaced apart electrodes forming a gap therebetween; and a controller configured to maintain a constant voltage between the electrodes during a first operating state and measure a current between the electrodes; wherein, if the controller detects a current above a threshold value during the first operating state, the controller is configured to increase a voltage between the electrodes during a second operating state.

In one embodiment, the controller may be configured to increase a voltage between the electrodes during the second operating state by 0.5-15% compared to the first operating state. After the voltage between the electrodes has been increased during the second operating state, the PM sensor may be configured to compare a measured change in current between the electrodes and a pre-determined value corresponding to a change in current of a resistive load in response to the increase in voltage. In another embodiment, if the measured change in current is less than the pre-determined value, a flag may be generated that the current detected above the threshold value is not plausible; and if the measured change in current is greater than the pre-determined value, a flag may be generated that the current detected above the threshold value is plausible. The pre-determined value corresponding to a change in current of a resistive load in response to the increase in voltage may include a calculated change in current increased by a multiplier.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
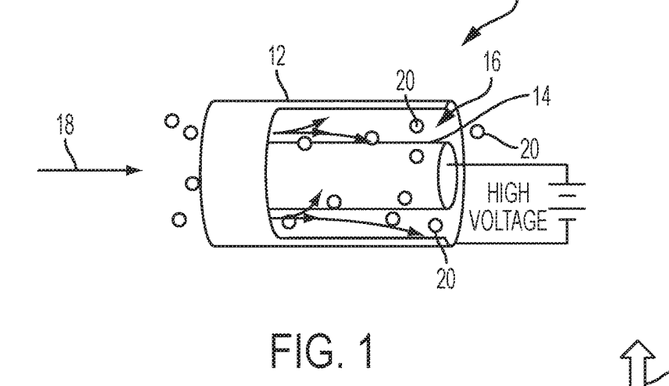
FIG. 1 is a partial cut-away view of an electrostatic particulate matter (PM) sensor, according to an embodiment.

With reference to FIG. 1, a partial cut-away of an electrostatic particulate matter (PM) sensor 10 is shown. The PM sensor 10 includes a first electrode 12 and a second electrode 14, which may be in parallel. The electrodes may be cylindrical and may be concentric. There may be an air gap 16 between the electrodes and a voltage may be maintained across the air gap 16 between the electrodes 12, 14. The voltage may create an electric field between the electrodes, the strength of which may be proportional to the potential. An exhaust stream 18 may enter the PM sensor 10 and pass between the electrodes in the direction shown. The exhaust stream may include particulate matter, such as soot particles 20. The soot particles 20 may have an electric charge, and may therefore stick or deposit on either the positive or negative electrode, depending on the charge of the particular particle. As described above, the soot particles 20 may accumulate over time and form dendrites, which may store a pooled charge. When the electrostatic force attracting the particles to the opposing electrode overcomes the force holding the dendrite together, the dendrite may break off and travel to the opposing electrode. When this occurs, the pooled charge may be measured as a current between the electrodes which may indicate the presence of soot in the exhaust stream and/or the rate at which it is entering the PM sensor 10.

While the PM sensor 10 may effectively detect the presence of soot, it may present a challenge for diagnostics, such as on-board diagnostics (OBD). Some regulations, such as CARB requirements, may require that vehicles include a method to diagnose faults in sensors, such as electrical shorts, wire breaks, or other faults that affect sensor performance. In its role as an exhaust filter monitor, the PM sensor 10 does not normally get exposed to soot as long as the filter is operating properly; therefore, there may be no sensor output that can be measured to evaluate the plausibility of the sensor reading, if there is conductivity between the electrodes and a sensor control module, and if the sensor is installed or remains in the exhaust pipe.

Figure 2:
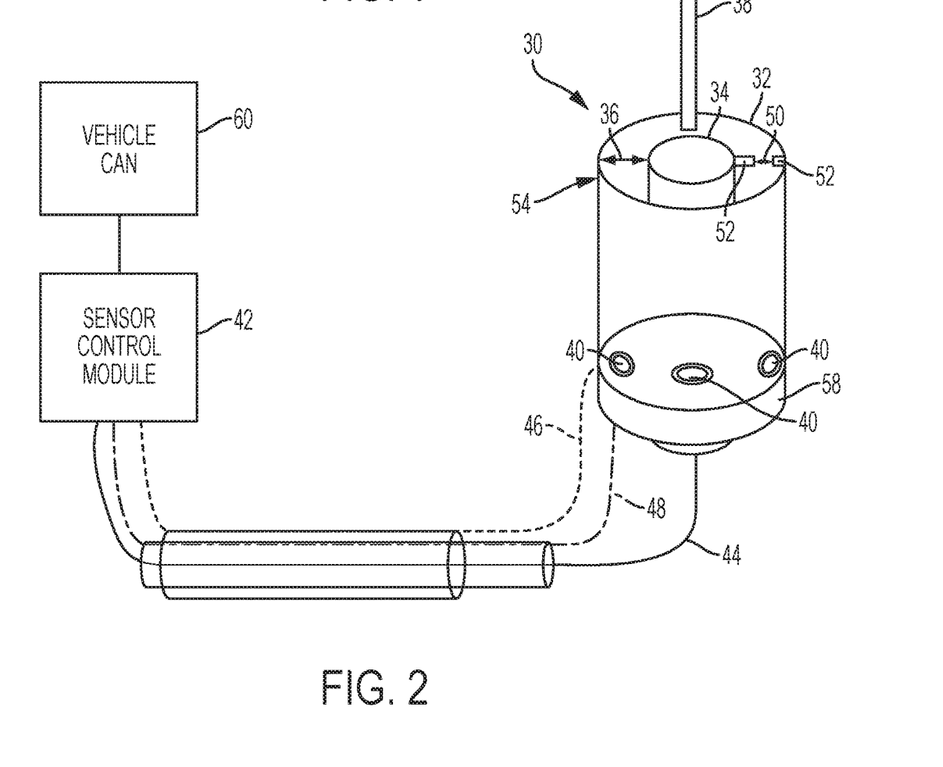
FIG. 2 is a schematic view of an electrostatic PM sensor including a reduced gap region, according to an embodiment.

With reference to FIG. 2, a PM sensor 30 is disclosed which may detect the presence of soot in the exhaust stream, but may also provide much-needed diagnostic information. The PM sensor 30 may perform any or all of the following three diagnostic tasks for an electrostatic PM sensor: 1) check continuity of the electrodes and associated wiring; 2) determine the plausibility of sensor output by differentiating the normal response to particulates from a faulty output associated with some kind of short circuit fault; and 3) check that the sensor has not fallen out of, or otherwise been removed from the exhaust pipe. As described in additional detail, below, these tasks may be achieved, at least in part, by actively varying the voltage applied to the electrodes and/or by providing the electrodes with a structure that is able to induce an electrical discharge at a specific location.

The PM sensor 30 may include spaced apart first and second electrodes 32 and 34, which may be in parallel. The electrodes may be cylindrical and may be concentric. In the embodiment shown, the first electrode 32 may be an outer electrode, which may be cylindrical, and the second electrode 34 may be an inner electrode, which may also be cylindrical, and the electrodes may be concentric. In one embodiment, the first electrode 32 may be the negative electrode and the second electrode 34 may be the positive electrode. However, the polarity may also be reversed. There may be an air gap 36 between the electrodes and a voltage may be maintained across the air gap 36 between the electrodes 32, 34. The voltage may create an electric field between the electrodes, the strength of which may be proportional to the potential. The voltage may be relatively high, such as at least 500 V or 750 V. In one embodiment, the voltage may be maintained at a constant or substantially constant voltage of between 500 V to 4,000 V, or any sub-range therein, during normal operation (e.g., steady state). For example, the voltage may be maintained at a constant voltage of between 500-3,000 V, 750-3,000 V, 750-2,500 V, 750-2,000 V, or 750-1,500 V. In one embodiment, the potential may be maintained at a constant voltage of about 1,000 V (1 kV). This constant voltage may be maintained for a majority of the time the PM sensor 30 is in use or active, for example, at least 75%, 85%, 90%, 95%, or 99% of the time. Stated another way, the constant voltage may be maintained unless the PM sensor 30 is undergoing a diagnostic test.

An exhaust stream may enter the PM sensor 30, pass between the electrodes, and exit the PM sensor 30 in the direction shown by arrow 38. The exhaust stream may be introduced into the PM sensor 30 in any suitable manner. In the embodiment shown, the exhaust stream may enter the PM sensor through one or more holes 40. The exhaust stream may include particulate matter, such as soot particles, as described above. The soot particles may have an electric charge, and may therefore stick or deposit on either the positive or negative electrode, depending on the charge of the particular particle.

The PM sensor 30 may be connected and/or in communication with a sensor control module (SCM) 42. The SCM 42 may be configured to control and change the voltage across the electrodes 32, 34. The SCM 42 may also be configured to perform other functions, such as the detection and measurement of current that passes between the electrodes 32, 34 and performing/controlling diagnostics (discussed in further detail, below). The SCM 42 may be connected to the PM sensor 30 by one or more wires or leads. In the example shown, there is a positive lead 44 connecting the SCM 42 to the positive electrode 34 and a ground lead 46 connecting the SCM 42 to the negative electrode 32. In addition, there may be a guard lead 48 that connects the SCM 42 to an insulator with a guard trace 58 that is attached or coupled to the PM sensor 30. The guard may be present so that any current leaking from the positive high voltage lead 44 to the negative lead 46 within the cables or non-sensing parts of the device may instead flow through the guard, which is in between the other two cables, and be compensated. This may prevent such leakage from being measured as a soot-mediated current. These three leads may be formed as a tri-axial cable. However, they may also be formed of separate, single cables or any combination of cables. Similarly, if there are fewer or greater number of leads, they may be formed as a single cable (e.g., four leads in a four-axis cable) or as a combination of smaller cables. The SCM 42 may be connected to other vehicle systems and controllers, for example, through a Controller Area Network (CAN bus) 60. The SCM 42 may send and/or receive controls to/from other processors or controllers in the vehicle (e.g., through CAN 60). The SCM 42 may include one or more controllers and/or may also send/receive data to/from other processors or controllers in the vehicle (e.g., through CAN 60).

With reference again to FIG. 2, the PM sensor 30 may include one or more reduced gap regions 50, which may also be referred to as localized gaps. As described above, an air gap 36 may be present between the electrodes. If the electrodes are parallel (e.g., concentric cylinders), the air gap 36 has a substantially constant size at every point in the PM sensor. For example, the air gap 36 may be defined as the length of a line that extends from one electrode to the other and is perpendicular to both. In the disclosed PM sensor 30, however, there may be one or more locations where one or both of the electrodes protrudes towards the other to form a reduced gap region 50. The air gap 36 may therefore include a bulk gap and one or more localized gaps. The bulk gap may be defined as the portion of the air gap 36 not including the localized gaps (e.g., reduced gap region(s) 50). The reduced gap regions 50, or localized gaps, may have a localized distance between the two electrodes that is smaller than a distance between the electrodes elsewhere in the air gap (e.g., the bulk gap distance).

The reduced gap region(s) 50 may be formed by protrusion(s) 52 extending from one or both of the electrodes 32, 34 to reduce the size of the air gap. The protrusion(s) 52 may be formed as part of (e.g., integral to) one of the electrodes or they may be attached or added to the electrodes after they are formed. If the protrusion(s) 52 are formed as part of the electrodes, they may be formed during the shaping or forming of the electrodes (e.g., by casting, forging, extrusion, stamping, etc.) or they may be formed at a later point (e.g., through a type of machining, stamping, or other deformation process). In these examples, the protrusion(s) 52 may be formed of the same material as the electrodes and may be formed as a single piece. If the protrusion(s) 52 are added or attached to the electrodes, they may be formed of a different material or the same material as the electrode to which they are attached. The protrusion(s) 52 may be attached in any suitable manner, such as welding, brazing, mechanical fastening (e.g., screws, rivets, etc.), or adhesives. In one embodiment, the protrusion(s) 52 may be electrically conductive. If additional material is used to attach the protrusion(s) 52 to the electrode(s), the material may also be electrically conductive (e.g., conductive adhesive, metal fasteners, etc.).

In the embodiment shown, there are two protrusions 52, one attached to each electrode, which extend toward each other to reduce the size of the air gap 36 to form a reduced gap region 50. However, in other embodiments, there may only be a single protrusion 52 that forms each reduced gap region 50, which may extend from either electrode to reduce the size of the air gap 36. In the embodiment shown in FIG. 2, there is a single reduced gap region 50, however, there may be two or more (e.g., a plurality of) reduced gap regions 50. In one embodiment, the reduced gap regions 50 may be equally spaced around a circumference of the electrodes. For example, if there are two reduced gap regions 50, they may be spaced 180 degrees from each other, if there are three reduced gap regions 50, they may be spaced 120 degrees from each other, and if there are four reduced gap regions 50, they may be spaced 90 degrees from each other, and so on. If there are multiple reduced gap regions 50, they may each be identical in terms of materials, method of attachment, size, and location (e.g., extending from one or both electrodes). However, the reduced gap regions need not be identical, and can have any combination of the properties described above.

In at least one embodiment, the reduced gap region(s) 50 may be located at or near a distal end 54 of the PM sensor 30. The distal end 54 may be defined as the end from which exhaust gas exits the PM sensor 30, or opposite the end at which exhaust gas enters the PM sensor 30. The distal end 54 may alternatively be defined as the end farthest from the wire attachments between the electrodes and the SCM 42 In one embodiment, the reduced gap region(s) 50 may be located within the last (e.g., most distal) 20% of the length of the electrodes, for example, the last 15%, 10% or 5% of the length of the electrodes. In one embodiment, if there are multiple reduced gap regions, they may be located at a same axial location (e.g., same distal length).

The reduced gap region(s) 50 may be used to cause an electrostatic discharge across the air gap 36 as a result of an electrical breakdown (or dielectric breakdown). An electrical breakdown is a decrease in the resistance of an electrical insulator when the voltage applied across it exceeds the insulator's breakdown voltage. As a result, the insulator may become momentarily electrically conductive, leading to an electrostatic discharge. In a gas, electrical breakdown may occur when the dielectric strength of the gas is exceeded. Air may undergo an electrical breakdown when it experiences a high voltage, for example, a voltage that generates an electric field strength of about 3 kV/mm. Accordingly, the voltage at which an electrical breakdown will occur for an air gap may be a function of the gap length, with a smaller gap making a discharge more likely (for a given voltage).

By creating a smaller air gap in the reduced gap region(s) 50, it may be possible to create an electrostatic discharge in a predetermined and known location. A voltage that would not otherwise cause a discharge at the original/non-reduced air gap 36 (e.g., distance between two parallel electrodes) may cause a discharge at the smaller air gap in the reduced gap region 50. Accordingly, by increasing the voltage to a level that is above the breakdown voltage of the reduced air gap but below the breakdown voltage for the original air gap, a discharge may be reliably and reproducibly generated at the reduced gap region(s) 50. In contrast, for a PM sensor that has only two concentric cylindrical electrodes, the air gap 36 is constant throughout the sensor. In this case, it may be difficult or impossible to predict where a discharge will occur since the breakdown voltage is substantially the same at every region of the sensor. In addition, the breakdown/discharge may occur in the cabling or the SCM, instead of the electrodes, if the breakdown threshold occurs at lower voltages in those components compared to the electrodes. Furthermore, by locating the reduced gap region(s) 50 at/near a distal end 54 of the PM sensor 30, it may be ensured that the discharge happens at/near the distal end.

The reduced gap region(s) 50 may reduce the size of the air gap 36 by a sufficient amount to significantly increase the likelihood that a discharge will occur at the reduced gap region 50 and not elsewhere in the air gap 36 (e.g., where the gap is larger and uniform). In one embodiment, the reduced gap region(s) may reduce the air gap 36 by at least 5%. For example, if the constant, uniform air gap between two electrodes is 1 mm, then the reduced gap region 50 may have a gap of 0.95 mm (950 microns). In another embodiment, the reduced gap region(s) may reduce the air gap 36 by at least 10%, 25%, 50%, 75%, 85%, 90%, or 95%. In one embodiment, the reduced gap region(s) may reduce the air gap 36 by 5-50%, or any sub-range therein.

As described above, the PM sensor 30 may be used to detect the presence of soot in the exhaust stream, while also allowing for any or all of the following diagnostics: 1) check continuity of the electrodes and associated wiring; 2) determine the plausibility of sensor output by differentiating the normal response to particulates from a faulty output associated with some kind of short circuit fault; and 3) check that the sensor has not fallen out of, or otherwise been removed from the exhaust pipe. These tasks may be achieved, at least in part, by actively varying the voltage applied to the electrodes and/or by providing the electrodes with a structure that is able to induce an electrical discharge at a specific location. The baseline soot detection operation of the PM sensor 30 may be referred to as a first operating state while the diagnostics may be referred to as a different operating state, such as a second, third, or fourth operating state.

Figure 3:
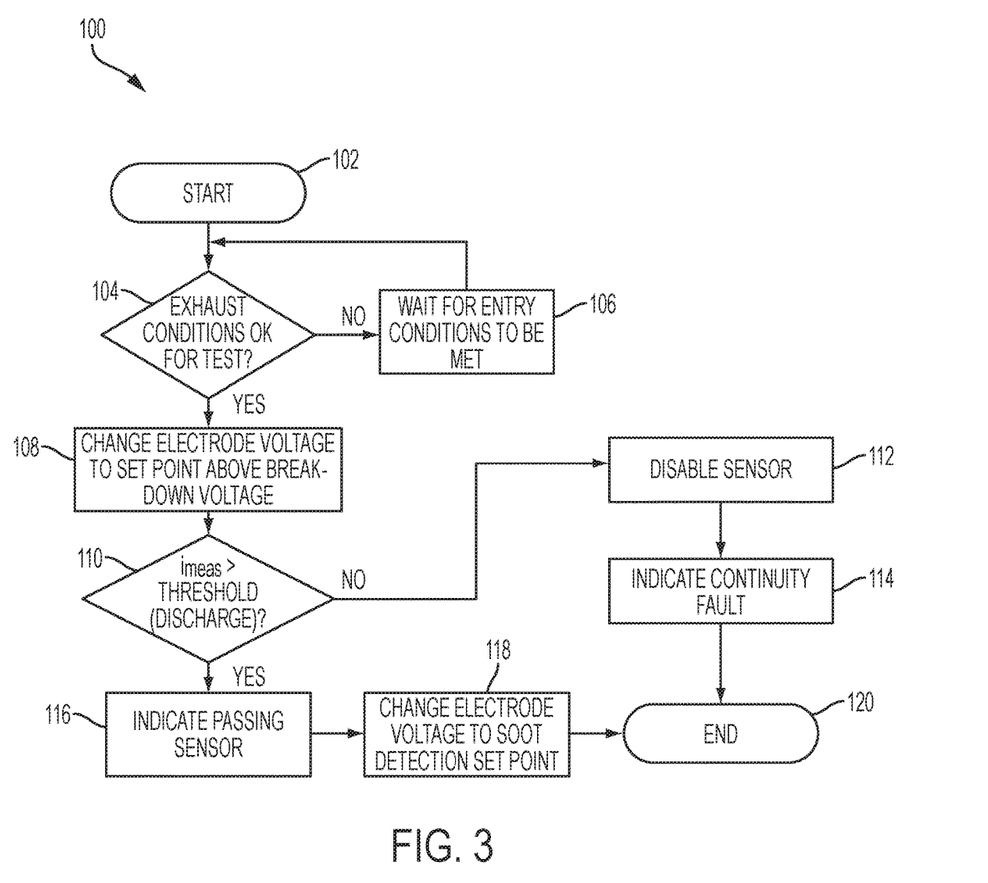
FIG. 3 is a flowchart of a continuity check diagnostic algorithm, according to an embodiment.

With reference to FIG. 3, an example of an algorithm 100 for performing a diagnostic that checks the continuity of the electrodes and associated wiring is shown. The algorithm 100 may be performed using a PM sensor, such as the PM sensor 30 described above and shown in FIG. 2. However, the algorithm 100 may also be performed on/using other PM sensors. The algorithm 100 may be used to determine whether the wiring, connectors/connections between the SCM and the PM sensor, and the electrodes themselves are in working order and that there is not an open circuit.

In step 102, the diagnostic test may be initiated. The diagnostic may be controlled or performed by the SCM or by another controller/processor that is connected to or in communication with the SCM. As described above, the PM sensor and SCM may be part of a vehicle exhaust system. Accordingly, the PM sensor and SCM may be in communication (directly or indirectly) with one or more vehicle controllers and vehicle systems, which may include a Controller Area Network (CAN bus). Accordingly, step 102 may be initiated by the SCM, or a controller connected thereto (directly or indirectly).

At step 104, it may be determined if the exhaust conditions are ok or acceptable to run the test. These conditions may include parameters such as exhaust temperature, exhaust flow rate, ambient temperature, and certain gas concentration levels, such as oxygen or NOx, or other conditions. These conditions may be measured at the PM sensor (e.g., by sensors included therein) or at other locations (e.g., upstream or downstream in the exhaust system or elsewhere in a vehicle). If it is determined that the conditions are not suitable to run the test, in step 106 the algorithm loops back to before step 104 to wait for the diagnostic to be initiated again.

At step 108, if the exhaust conditions are acceptable from step 104, the electrode voltage is changed to a value above the breakdown voltage of the air gap in the PM sensor. The voltage may be changed or adjusted by the SCM. The change may be a step change (e.g., instantaneous or near-instantaneous) or a gradual/continuous change (e.g., at a constant rate or a curved/exponential rate). Prior to the diagnostic test being run, the voltage may be held constant at a pre-determined value, such as around 1 kV. During step 108, the voltage may be increased above the constant value to a level that is calculated to be above the breakdown voltage of the air gap in the PM sensor. The increased voltage set point may be determined based on the properties/configuration of the particular PM sensor and the exhaust stream, such as the size of the air gap, exhaust stream temperature, or others. In embodiments where there the PM sensor includes a reduced gap region between the two electrodes, the breakdown voltage may be lower than a breakdown voltage needed to cause a discharge across the original/normal air gap (e.g., non-reduced regions).

In one embodiment, the change in voltage across the electrodes may be at least a 10% increase from the pre-diagnostic voltage (e.g., the constant voltage maintained in the PM sensor during normal operation). In another embodiment, the change in voltage across the electrodes may be at least a 25%, 50%, 75%, 100%, or 200% increase from the pre-diagnostic voltage (e.g., 1.25×, 1.5×, 1.75×, 2×, or 3×). In one embodiment, the constant, pre-diagnostic voltage may be from 0.75 to 1.5 kV. In this embodiment, the changed voltage during step 108 may be greater than the pre-diagnostic voltage and be from 1.25 to 5 kV, or any sub-range therein, such as 1.5 to 4 kV or 2 to 4 kV.

In step 110, the electrodes are monitored for a change in current that indicates a discharge due to an electrical breakdown. During normal operation, there is little or no current passing between the electrodes. However, if a discharge occurs, there should be a nearly instantaneous spike in current. Based on the properties of the PM sensor and the voltage being applied, a threshold current level may be determined that is at or below the current indicative of a discharge but above any background noise in the current signal. Accordingly, if, as a result of the change in voltage in step 108, there is electrostatic discharge, then a nearly instantaneous spike in current should be measured that is above the calculated threshold value. In embodiments where the PM sensor includes a gap reduction region, the discharge should occur at the gap reduction region and not at a region upstream from the gap reduction region. If the gap reduction region is located at a distal end of the PM sensor, then it can be determined that all wiring, circuitry, electrodes, etc. upstream of the gap reduction region were involved in the discharge (or lack thereof, depending on the determination in step 110).

In step 112, if it is determined that there was no current spike as a result of the increased voltage in step 108, or at least no current spike that exceeds the threshold value, then it is determined that there is some sort of fault or defect in the electronics of the PM sensor. This may be due to faulty wiring, and open/incorrect connection, a defect in the electrodes themselves, a short circuit, or other potential reasons. The voltage between the electrodes may also be monitored during steps 108 and 110 in order to ensure that the determination in step 110 is accurate. For example, if a certain amount of current flows due to short circuit conditions, the voltage may not rise to the desired level. Alternatively, if a short circuit occurred through the guard wire, there may not be a significant increase in current measured between the electrode pair. Accordingly, the voltage may also be monitored during the diagnostic (e.g., at steps 108 and/or 110) to confirm an accurate determination. As a result, in step 112, the PM sensor may be disabled. The sensor may be disabled because it is no longer reliable, to avoid further damage to itself or other systems due to the detected fault, and/or to prevent other systems from relying on data provided by the sensor, or other possible reasons.

In step 114, the detection of the fault or defect in the PM sensor may be communicated or indicated to the vehicle driver and/or to other vehicle system components. For example, an indicator light may be illuminated in the vehicle cabin, for example, on the dashboard or the instrument panel, to alert the driver or occupant that there is an issue. In addition to, or instead of, notifying the occupants of the vehicle, a message may be sent to one or more vehicle systems to alert them of the fault. This may allow any systems that rely on or utilize data from the PM sensor to ignore or cut-off communication from the PM sensor that may not be accurate.

In step 116, if it is determined that there was a current spike as a result of the increased voltage in step 108 that exceeds the threshold value, then it is determined that the sensor is working properly, at least from an electrical standpoint. In embodiments where a gap reduction region is located at a distal end of the PM sensor, it can be determined that all wiring, circuitry, electrodes, etc. upstream of the gap reduction region are working properly. Accordingly, placing one or more gap reduction regions at the distal end of the PM sensor may ensure that all electronics and components are included in the diagnostic test and a positive result in step 116 indicates that the entire system is in working order.

In step 118, the changed/increased voltage from step 108 is reduced to a soot detection level. In one embodiment, the voltage may be returned to the same level prior to the diagnostic algorithm 100 being performed (e.g., the constant, pre-determined value, such as around 1 kV). The change may be a step change (e.g., instantaneous or near-instantaneous) or a gradual/continuous change (e.g., at a constant rate or a curved/exponential rate). Once the voltage is lowered or returned to its previous value, the PM sensor can continue to operate as a soot detector.

In step 120, the diagnostic algorithm may be ended, either as a result of a passing indication (step 116) or a fault indication (step 114). At the end of the diagnostic, the outcome may be stored in memory (e.g., in the SCM or elsewhere in the vehicle electronics). In addition to, or instead of, storing the outcome, the outcome may be communicated to an external system outside of the vehicle, for example, to the owner/driver, to the vehicle manufacturer or dealer, or to a network-based system (e.g., an online cloud-based system). The communication may be made using any suitable method or protocol, such as wi-fi, cellular, Bluetooth, SMS or other messaging services, email, NFC, or others.

Figure 4:
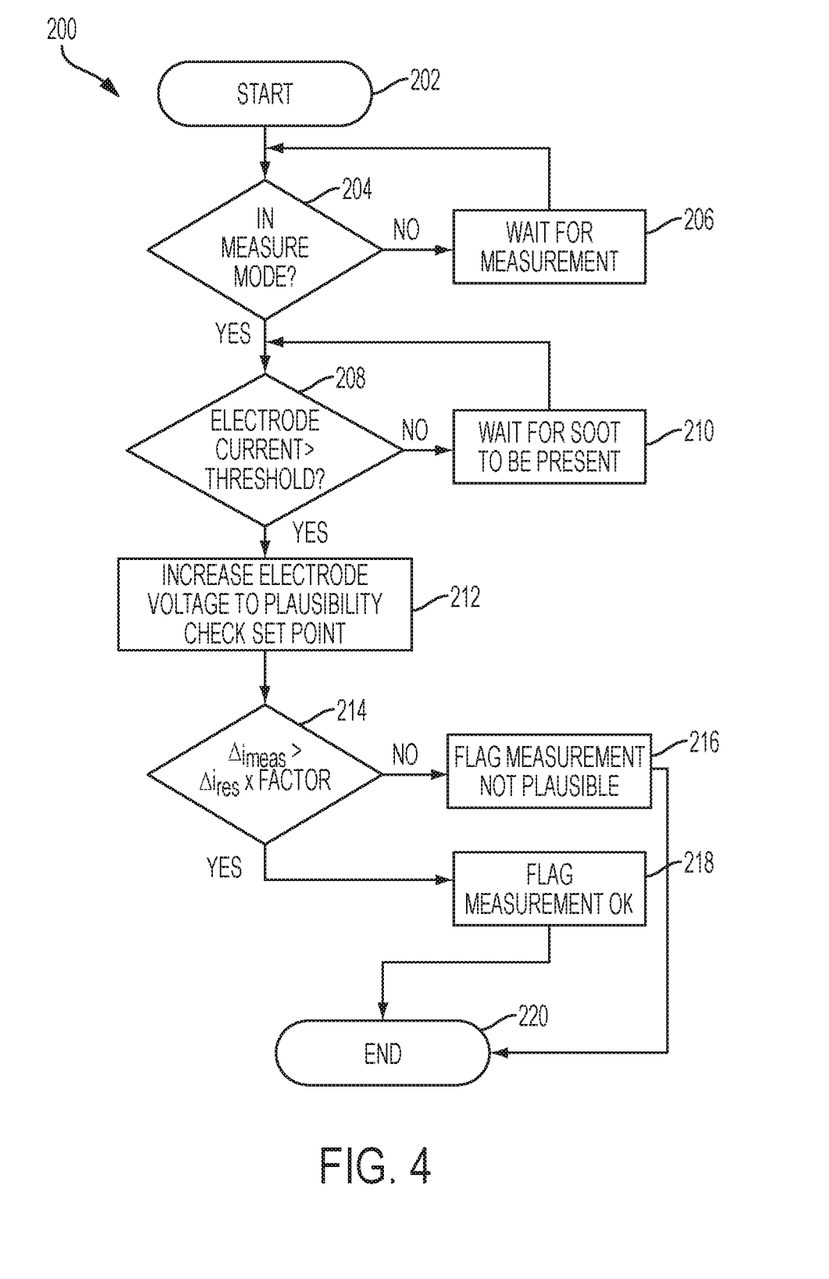
FIG. 4 is a flowchart of a soot measurement plausibility algorithm, according to an embodiment.
Figure 5A:
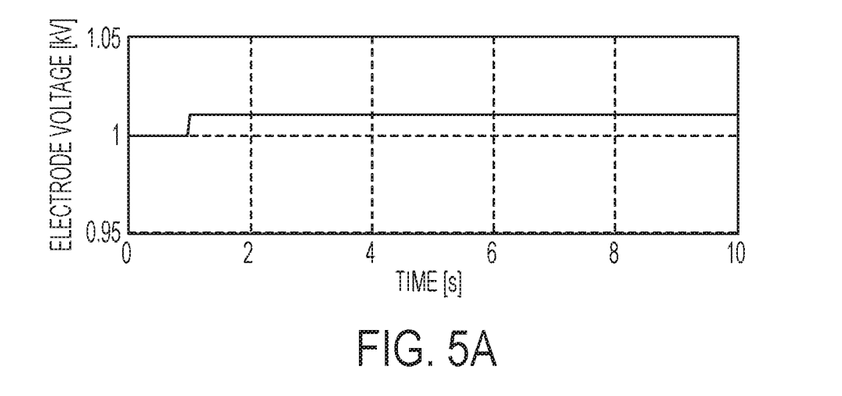
FIG. 5A is an example of a voltage vs. time plot showing a step increase in voltage between two electrodes.
Figure 5B:
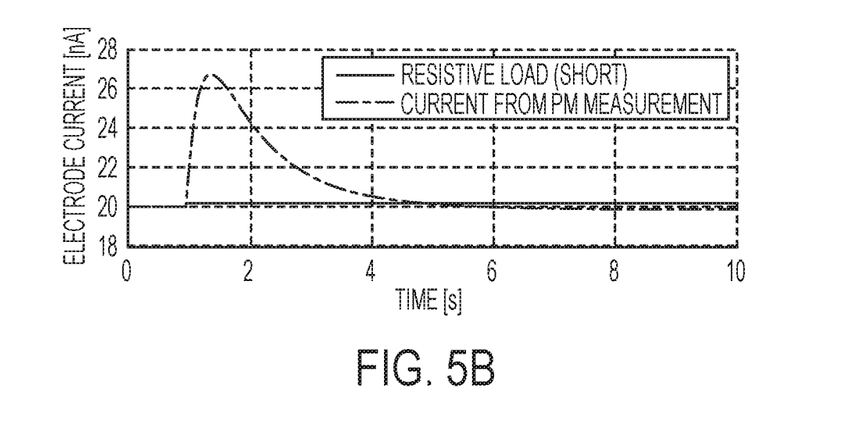
FIG. 5B is an example of a current vs. time plot showing the different responses of soot and a resistive load to the voltage change in FIG. 5A.

With reference to FIGS. 4, 5A, and 5B, an example of an algorithm 200 is shown for performing a diagnostic that checks the plausibility of sensor output by differentiating the normal response to particulates from a faulty output associated with some kind of short circuit fault. The plausibility algorithm 200 may be performed using a PM sensor, such as the PM sensor 30 described above and shown in FIG. 2. However, the plausibility algorithm 200 may also be performed on/using other PM sensors. The algorithm 200 may be used to make sure that spikes in current seen by the PM sensor are, in fact, due to the presence of soot in the exhaust stream and not some other source.

In step 202, the diagnostic test may be initiated. The diagnostic may be controlled or performed by the SCM or by another controller/processor that is connected to or in communication with the SCM. As described above, the PM sensor and SCM may be part of a vehicle exhaust system. Accordingly, the PM sensor and SCM may be in communication (directly or indirectly) with one or more vehicle controllers and vehicle systems, which may include a Controller Area Network (CAN bus). Accordingly, step 102 may be initiated by the SCM, or a controller connected thereto (directly or indirectly).

In step 204, the diagnostic determines whether the PM sensor is in a current measuring mode. The current measuring mode monitors the current between the electrodes in the PM sensor. If the PM sensor is not in the current measuring mode, then, in step 206, the diagnostic may loop back to step 204 and wait for the PM sensor to be in current measuring mode. Non-limiting reasons for the PM sensor to not be in measuring mode may include non-suitable or non-ideal conditions in the exhaust system (e.g., temperature, flow, etc.) or the PM sensor may be performing a different diagnostic.

In step 208, if the PM sensor is in a current measuring mode, and it detects a current between the electrodes, then it may compare the detected current to a threshold current value. As described above, a current may be detected when a soot dendrite builds up and then breaks off and transports to the opposite electrode. The dendrite may transfer its pooled charge (generally on the order of nano-amps) to the opposite electrode, which may be detected as a current between the two electrodes. Accordingly, if a current is detected between the two electrodes, it may be an indication that soot is present in the exhaust and has begun to build up in the PM sensor. In step 208, a measured current may be compared to a threshold current value to determine if a potential soot break-off has occurred. The threshold current value may be set at a value corresponding to a typical or average current generated by a broken-off dendrite. Alternatively, the threshold may be set to a value below the typical value in order to detect most or all dendrite break-offs (e.g., a safety factor).

In step 210, if either no current is detected in step 208 or a current is detected that is below the threshold current value, then the algorithm may loop back to before step 208 and wait for new or additional current measurements. A "no" indication from step 208 essentially means that either no soot is present or an insufficient amount of soot has accumulated and broken off to generate a current above a minimum threshold. Therefore, a "no" indication in step 208 is not necessarily an indication that no soot is present in the exhaust stream. However, it is an indication that soot has not built-up enough to cause significant dendrite break-off.

In step 212, if there is a current measured in step 208 that is above the threshold value, then the plausibility check may be initiated. In this step, the voltage between the PM sensor electrodes may be increased from its normal, constant voltage value (e.g., prior to the diagnostic beginning). The voltage increase may be a step increase, such that is instantaneous or substantially instantaneous. The voltage between the electrodes may be increased in order to assess or analyze the current response to the change in voltage.

With reference to FIGS. 5A and 5B, example plots are shown of voltage vs. time and corresponding current vs. time for two different responses to a change in voltage. FIG. 5A shows an example of a step change in voltage from 1 kV to 1.01 kV at t=1s, or a 1% increase in voltage. FIG. 5B shows the current response to the step change in voltage for a charge transfer due to dendrites (dotted) and for a resistive load (solid). For a resistive load between the electrodes (e.g., a short circuit or other current leak path) the current will be directly proportional to the voltage according to Ohm's law, where $$\frac{V}{i} = R.$$

This means that for a 1% increase in voltage, the current should increase by 1% for a purely resistive load.

For soot particles participating in the charge transfer mechanism in the sensor, however, the variation in current observed from this transfer will not be proportional to the voltage change, but will be transient. Because the operation of the electrostatic PM sensor relies on a balance of forces between those that hold the soot particles to the surface of the electrode and the electrostatic forces that pull it toward the opposite electrode, any upset to the balance between those forces may cause a sudden change in the dendrites that form as soot accumulates on the electrodes. Such change in the dendrites leads to more or less transfer of charge from one electrode to the other. If the voltage is increased, the force due to the electric field becomes stronger, which may cause a sudden break-off of more dendrites. This sudden break-off will transfer charge to the opposing electrode, yielding a spike in current of a much larger magnitude than what would be expected for a resistive load. This spike also dissipates as the balance of sticking and electric forces achieve a new equilibrium.

FIG. 5B shows this sudden spike in current from a step increase in voltage. As shown, the current represented by the dotted line sharply (but not instantly) increases when the step change in voltage appears. The current continues to rise for a few tenths of a second and then peaks. After peaking, the current gradually declines back to its previous levels, or slightly below, over a course of several seconds. The sharp increase is caused by the sudden change in voltage, however, not all of the dendrites may break-off at once, some may take longer than others. Accordingly, the change in current is more of a curve than a step. In addition, once all the dendrites that are of the right charge status (or greater) have broken off, there are no dendrites left to break-off and the current dips back to its previous level (e.g., the spike is transient, not persistent). In contrast, if the current response is that of a resistive load (solid line), then the increased voltage will result in a proportional increase in current that persists until the voltage is changed. In addition, as described above, the peak current of the transient curve (dendrites) is greater than the change in current from a resistive load by a substantial margin.

Accordingly, by analyzing the current response from the increased voltage of step 212, it may be possible to determine if the current detected in step 208 is from soot or from some type of resistive load. While the above step is described with regards to increasing the voltage, it may also be possible to conduct the test by decreasing the voltage. If the voltage is decreased, the dendrites may stop breaking off and need to grow longer before the electric field can break them off and pull charge to the other electrode. This may result in a transient dip in current much larger than what would result from reducing the voltage across a resistive load. Therefore, the plots of a reduced voltage may look like vertically flipped versions of FIGS. 5A and 5B.

The voltage change (increase or decrease) in step 212 can be relatively small and still produce the described transient current reading. In one embodiment, the voltage change may be at least 0.5% of the normal operating voltage (e.g., pre-diagnostic voltage). For example, if the normal, constant voltage is 1 kV, the changed voltage may be at least 1.005 kV or no greater than 0.995 kV. In another embodiment, the voltage change may be at least 1% of the normal operating voltage, for example, at least 2%, 3%, 5%, or 10% of the normal operating voltage. In one embodiment, the voltage change may be from 0.5-15% of the normal operating voltage, or any sub-range therein, such as 0.5-10%, 0.5-8%, 0.5-5%, 0.5-3%, or 0.75-2% of the normal operating voltage. In one embodiment, the voltage change may be about 1% of the normal operating voltage. These relatively small changes are examples, however, and are not intended to be limiting. For example, higher or lower voltage changes may also be used to achieve similar results. In general, the operating voltage may be increased to any level below which a dielectric breakdown may occur.

In step 214, the change in current that is measured in response to the voltage change in step 212 is compared to an expected change in current that would occur for a resistive load (e.g., based on Ohm's law). For example, a 1% increase in voltage would be expected to result in a roughly 1% increase in current for a resistive load. However, as described above, the change in current for a sudden break-off of dendrites is generally substantially larger than the proportional increase of a resistive load. Accordingly, if the measured change in current is greater than the expected change for a resistive load, the original soot detection in step 208 is plausible, because a change in voltage resulted in additional dendrites breaking-off. The measured change in current may be the peak or max change in current (e.g., the peak shown in FIG. 5B). In addition, or as an alternative, to measuring the change in current value, step 214 may compare other characteristics of the current change in response to the voltage increase. For example, as shown and described with respect to FIG. 5B, if a transient current change is detected then it may be an indication of a plausible soot detection.

In order to make a positive determination more robust, the expected change in current for a resistive load may be multiplied by a factor (e.g., safety factor) and then compared to the measured current change. The factor may be greater than 1 such that it increases the expected current change, for example, it may be 2, 3, 4, 5, 10, 15, or another integer. In one embodiment, the factor may be at least 5. However, any real number greater than 1 may be used depending on the degree of certainty desired. But, the factor should not be so high that it risks increasing the expected current change to a value similar to the change in current from a sudden dendrite break-off.

In step 216, if the measured current change is not greater than the expected current change for a resistive load (alone or multiplied by safety factor), then the measurement in step 208 may be flagged as a non-plausible soot detection. This may mean that there is some sort of short-circuit or other fault in the circuitry, or it may be a random or anomalous event. Similar to step 114 in algorithm 100 above, the flagging of the non-plausible measurement may be communicated or indicated to the vehicle driver and/or to other vehicle system components. For example, an indicator light may be illuminated in the vehicle cabin, for example, on the dashboard or the instrument panel, to alert the driver or occupant that there is an issue. In addition to, or instead of, notifying the occupants of the vehicle, a message may be sent to one or more vehicle systems to alert them of the issue. This may allow any systems that rely on or utilize data from the PM sensor to ignore or cut-off communication from the PM sensor that may not be accurate.

In step 218, if the measured current change is greater than the expected current change for a resistive load (alone or multiplied by safety factor), then the measurement in step 208 may be flagged as a plausible soot detection. While the measurement may be determined to be plausible, it may not be a complete guarantee that the measurement was a soot detection. However, the initial detection, followed by a current response representative of soot dendrite break-off after a voltage change, is a strong indication that the original detection was accurate. Similar to step 216, the plausibility of the measurement may be communicated or indicated to the vehicle occupants and/or vehicle systems.

In step 220, after the measurement in step 208 has been identified as either plausible or non-plausible, the diagnostic may be ended. Similar to step 120 in algorithm 100, the outcome may be stored in memory (e.g., in the SCM or elsewhere in the vehicle electronics). In addition to, or instead of, storing the outcome, the outcome may be communicated to an external system outside of the vehicle, for example, to the owner/driver, to the vehicle manufacturer or dealer, or to a network-based system (e.g., an online cloud-based system). The communication may be made using any suitable method or protocol, such as wi-fi, cellular, Bluetooth, SMS or other messaging services, email, NFC, or others.

Figure 6:
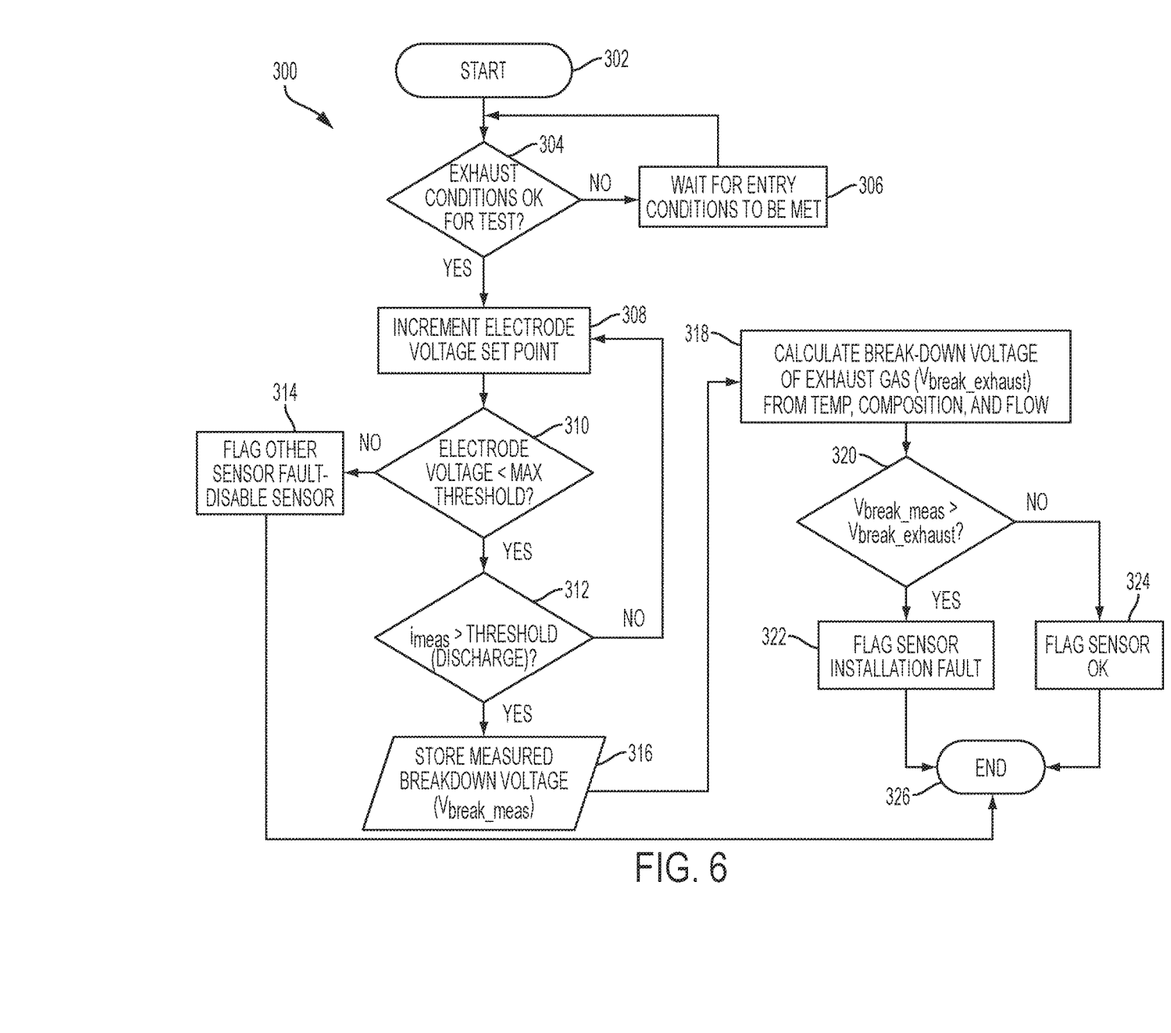
FIG. 6 is a flowchart of an installation algorithm, according to an embodiment.

With reference to FIG. 6, an example of an algorithm 300 is shown for performing a diagnostic that checks that the PM sensor is still installed and has not fallen out or been removed (intentionally or unintentionally). The installation algorithm 300 may be performed using a PM sensor, such as the PM sensor 30 described above and shown in FIG. 2. However, the installation algorithm 300 may also be performed on/using other PM sensors. The algorithm 300 may be used to make sure that the PM sensor has not become dislodged from the vehicle exhaust system or fallen out of the vehicle entirely. The algorithm 300 may also be used to detect if the sensor has been removed intentionally by a person. In general, algorithm 300 includes evaluating the voltage at which break-down across the electrodes occurs and comparing that to the expected break-down voltage for the conditions in the exhaust. Based on the relationship between breakdown voltage and temperature, it may be determined whether the PM sensor is properly installed in the exhaust pipe.

In step 302, the diagnostic test may be initiated. The diagnostic may be controlled or performed by the SCM or by another controller/processor that is connected to or in communication with the SCM. As described above, the PM sensor and SCM may be part of a vehicle exhaust system. Accordingly, the PM sensor and SCM may be in communication (directly or indirectly) with one or more vehicle controllers and vehicle systems, which may include a Controller Area Network (CAN bus). Accordingly, step 302 may be initiated by the SCM, or a controller connected thereto (directly or indirectly).

At step 304, it may be determined if the exhaust conditions are ok or acceptable to run the test. These conditions may include parameters such as exhaust temperature, exhaust flow rate, ambient temperature, and certain gas concentration levels, such as oxygen or NOx, or other conditions. These conditions may be measured at the PM sensor (e.g., by sensors included therein) or at other locations (e.g., upstream or downstream in the exhaust system or elsewhere in a vehicle). If it is determined that the conditions are not suitable to run the test, in step 306 the algorithm loops back to before step 304 to wait for the diagnostic to be initiated again.

In step 308, the voltage between the electrodes of the PM sensor may be increased over time. The voltage may be begin at the normal operating voltage, such as the constant voltage that was maintained prior to running the diagnostic (e.g., about 1 kV). The voltage may be increased by the SCM. In one embodiment, the voltage increase may be a continuous or constant increase (e.g., linear). For example, the voltage may be increased at a rate of 1 V/s, 5 V/s, 10 V/s, or any other suitable rate. In another embodiment, the voltage may be increased in a step-wise manner with distinct jumps or increases in voltage separated by a period of constant voltage. The voltage may be increased at any suitable interval, for example, each step increase may be 1 V, 5 V, 10 V, 20 V, or other values. In one embodiment, the step increase may be from 1 to 50 V, or any sub-range therein, such as 5 to 40 V, 5 to 25 V, 5 to 15 V, or about 10 V. Each step during the increase may be the same size, or the steps may change in size as step 308 continues (e.g., steps get larger over time or smaller over time).

In step 310, the voltage may be increased in step 308 up until a pre-determined max voltage level. This level may be set at a value at which a discharge should have occurred between the PM sensor electrodes. The max voltage value, or threshold value, may be set using a safety factor or multiplier. For example, if it is expected that a discharge should occur at 1.3 kV or less, a safety factor of 2 would result in the threshold voltage being 2.6 kV. The safety factor or multiplier may be set to any suitable value based on the design considerations and the knowledge of one or ordinary skill in the art, based on the present disclosure. Accordingly, in step 310, it is determined whether the voltage increases from step 308 have reached the threshold value (or exceeded it).

In step 312, if the incremented voltage from step 308 is below the threshold voltage, then a measured current between the electrodes of the PM sensor is compared to a threshold current that is indicative of an electrostatic discharge between the electrodes. During normal operation, there is little or no current passing between the electrodes. However, if a discharge occurs, there should be a nearly instantaneous spike in current. Based on the properties of the PM sensor and the voltage being applied, a threshold current level may be determined that is at or below the current indicative of a discharge but above any background noise in the current signal. Accordingly, if, as a result of the change in voltage in step 308, there is electrostatic discharge, then a nearly instantaneous spike in current should be measured that is above the calculated threshold value. Alternately, if the current limit of the power supply is reached, a voltage drop in response to a breakdown event may be observed. In embodiments where the PM sensor includes a gap reduction region, the discharge should occur at the gap reduction region and not at a region upstream from the gap reduction region.

The current measurements compared in step 312 may be continuous or periodic, similar to the voltage increases in step 308. For example, if the voltage increases constantly or continuously, the current measurement may be, also. Alternatively, the current may be measured on a periodic basis, such as once per second, once every 5 seconds, etc. In another embodiment, the current may be measured when there is a change in voltage. For example, if the voltage in step 308 is changed in a step-wise manner, every time there is a step change the current may be measured. In addition, other current measuring schedules may be utilized.

If the current measured in step 312 is not greater than the threshold voltage (e.g., no discharge), then the algorithm may loop back to step 308 and the voltage may be increased again (or continue to constantly increase). In one embodiment, the increases in voltage in step 308 may occur only after the comparison in step 312 is performed. In other embodiments, the increases may continue regardless of whether step 312 has been performed (but may be ceased if a yes indication is received).

In step 314, if the measured current in step 312 continues to not exceed the threshold voltage and the voltage increase in step 308 ultimately exceeds the max voltage threshold in step 310, then a fault may be flagged. This occurrence indicates that no discharge occurred despite increasing the voltage between the electrodes a level at which a discharge should have occurred or to a voltage that is potentially dangerous or harmful to the system. As a result, in step 314, the PM sensor may be disabled. The sensor may be disabled because it is no longer installed properly, it is damaged, to avoid further damage to itself or other systems due to the detected fault, and/or to prevent other systems from relying on data provided by the sensor, or other possible reasons.

In step 314, the detection of the fault or defect in the PM sensor may be communicated or indicated to the vehicle driver and/or to other vehicle system components. For example, an indicator light may be illuminated in the vehicle cabin, for example, on the dashboard or the instrument panel, to alert the driver or occupant that there is an issue. In addition to, or instead of, notifying the occupants of the vehicle, a message may be sent to one or more vehicle systems to alert them of the fault. This may allow any systems that rely on or utilize data from the PM sensor to ignore or cut-off communication from the PM sensor that may not be accurate. The outcome may be stored in memory (e.g., in the SCM or elsewhere in the vehicle electronics). In addition to, or instead of, storing the outcome, the outcome may be communicated to an external system outside of the vehicle, for example, to the owner/driver, to the vehicle manufacturer or dealer, or to a network-based system (e.g., an online cloud-based system). The communication may be made using any suitable method or protocol, such as wi-fi, cellular, Bluetooth, SMS or other messaging services, email, NFC, or others.

In step 316, if the current measured between the electrodes in step 312 is greater than the threshold voltage (indicating a discharge), then the voltage level at which the discharge (electrical breakdown) occurred may be stored. The voltage level may be stored in memory (e.g., in the SCM or elsewhere in the vehicle electronics). In addition to, or instead of, storing the outcome, the outcome may be communicated to an external system outside of the vehicle (at which it may be stored). For example, the voltage level may be sent to the owner/driver, to the vehicle manufacturer or dealer, or to a network-based system (e.g., an online cloud-based system). The communication may be made using any suitable method or protocol, such as wi-fi, cellular, Bluetooth, SMS or other messaging services, email, NFC, or others.

In step 318, a breakdown voltage of the exhaust gas may be calculated. The calculation may be based on conditions or parameters of the PM sensor, conditions or properties of the exhaust gas, environmental/ambient conditions, or other factors that may affect the breakdown voltage. Non-limiting examples of potential factors may include the temperature of the exhaust gas, composition of the exhaust gas, the flow rate of the exhaust gas, the presence of and/or the configuration of a gap reducing region in the PM sensor (e.g., the size of the reduction), or the ambient temperature. Accordingly, the breakdown voltage calculated in step 318 should estimate or approximate the voltage at which breakdown should occur in the PM sensor. The calculation may be performed by the SCM or any other processor/controller in the vehicle.

In step 320, the voltage level stored in step 316 is compared to the calculated voltage level from step 318. This comparison may indicate whether the PM sensor is located or installed in the correct position or if it has shifted (e.g., farther downstream or out of the vehicle). Breakdown voltage generally varies as a function of temperature. It is inversely related to temperature, such that it decreases with increasing temperature and increases with decreasing temperature. A sensor that is not properly installed in the exhaust pipe, either shifted downstream or fallen out of the exhaust system, would be cooler than a normal sensor. Therefore, such a dislodged sensor would have a higher breakdown voltage than a sensor that is still located in the correct position. By comparing the voltage at which the breakdown actually occurred to the calculated breakdown voltage, it can be determined whether the sensor is still in its correct position. Similar to the threshold values described above, the calculated breakdown voltage may have a multiplier or safety factor built in, or a multiplier may be applied after the voltage is calculated, to ensure that a positive result is truly due to a displaced sensor.

In step 322, if the measured breakdown voltage is higher than the calculated voltage (with or without a multiplier), then it is an indication that the sensor has either been displaced farther downstream in the exhaust system or has potentially fallen out of the system altogether (e.g., dangling by wires). In this case, an installation fault flag may be generated. Similar actions may be taken based on the fault as those described in step 314, such as an indicator light being generated, the flag being stored or communicated to another system, or the sensor being deactivated.

In step 324, if the measured breakdown voltage is not higher than the calculated voltage (with or without a multiplier), then it is an indication that the sensor is still in the correct location. In this case, an installation correct or "OK" flag may be generated. Similar actions may be taken based on the OK flag as those described in steps 314 and 322, except that generally the sensor will not be disabled and other systems will continue to communicate with and use data from the sensor.

After steps 314, 322, or 324, the diagnostic may be ended in step 326. If not already done so (or again), the result of the diagnostic may be stored in memory (e.g., in the SCM or elsewhere in the vehicle electronics). In addition to, or instead of, storing the outcome, the outcome may be communicated to an external system outside of the vehicle (at which it may be stored). For example, the voltage level may be sent to the owner/driver, to the vehicle manufacturer or dealer, or to a network-based system (e.g., an online cloud-based system). The communication may be made using any suitable method or protocol, such as wi-fi, cellular, Bluetooth, SMS or other messaging services, email, NFC, or others.

While the installation algorithm 300 may be performed a single time to determine whether the sensor is still installed, it may alternatively be performed multiple times under different conditions. Running the diagnostic multiple times under different conditions may provide an increased level of certainty that the PM sensor is either still installed properly or has been dislodged/removed. In one embodiment, the different conditions under which the algorithm 300 may be run multiple times may be exhaust gas temperature. In general, the temperature of vehicle exhaust gas will vary depending on factors such as how long the engine has been running or the operating conditions of the engine (e.g., driving at faster or slower speeds). Accordingly, the algorithm 300 may be performed two or more times when significantly different exhaust gas temperatures are present.

The exhaust gas temperature tends to be at its lowest at vehicle start-up, or shortly thereafter. Therefore, the algorithm 300 may be performed at start-up or within a certain (relatively short) time from start-up to compare the measured breakdown voltage to the calculated breakdown voltage at a relatively low exhaust gas temperature. As the engine heats up, the exhaust gas temperature generally increases. Accordingly, after a certain period of time, such as a few minutes, the algorithm 300 may be performed again to compare the measured breakdown voltage to the calculated breakdown voltage at a relatively high exhaust gas temperature. The algorithm 300 may be performed multiple times at multiple different exhaust gas temperatures, for example, two, three, four, or more temperatures. If the PM sensor is properly installed and in the correct position, the outcome should be that the measured breakdown voltage is less than the calculated breakdown voltage (possibly with a multiplier). The algorithm 300 may be configured such that if a certain minimum number or percentage of the comparisons in step 320 come back "no" then the sensor is flagged "OK" (step 324) and if less than the minimum come back "no" then the sensor is flagged as faulty (step 322). For example, if the algorithm is run three times, then for the sensor to be flagged "OK" it may have to meet the condition of step 320 at least two out of three times. A similar approach of running the diagnostic multiple times may also be applied to algorithms 100 and 200. As described above, any of the flagging or indication steps may be triggered based on a certain number or percentage of the total outcomes.

While examples of algorithms 100, 200, and 300 have been shown and described herein, the specific order of the steps is not limited to those shown and described, and one of ordinary skill in the art will understand that, based on the present disclosure, certain steps may be rearranged. In addition, certain steps may be omitted or without affecting the result of the diagnostics. Additional steps may also be included in the diagnostics without departing from the disclosed systems and methods. As described above, the disclosed algorithms may be performed on or using a PM sensor having one or more reduced gap regions. However, the algorithms may also be performed on or using other PM sensors, including those without a reduced gap region. The disclosed PM sensors and algorithms may be used in a vehicle exhaust system, including diesel or gasoline-powered vehicles. However, any application in which PM or soot detection sensors are used may be improved using the disclosed PM sensor and/or algorithms.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. An electrostatic particulate matter (PM) sensor, comprising:
    first and second spaced apart electrodes forming a bulk gap therebetween having a bulk distance and a localized gap therebetween having a localized distance less than the bulk distance; and
    a controller configured to maintain a voltage between the electrodes that is constant during a first operating state and to increase the voltage between the electrodes during a second operating state to induce an electrostatic discharge at the localized gap if there are no electrical faults in the PM sensor.

2. The PM sensor of claim 1, wherein the controller is configured to increase the voltage between the electrodes to at least 50% above the constant voltage of the first operating state.

3. The PM sensor of claim 1, wherein the localized gap is formed by a protrusion extending from one of the first or second electrodes towards the other.

4. The PM sensor of claim 3, wherein the localized gap is formed by a protrusion extending from each of the first and second electrodes towards the other.

5. The PM sensor of claim 3, wherein the protrusion is integrally formed with the electrode from which it extends.

6. An electrostatic particulate matter (PM) sensor, comprising:
    first and second spaced apart electrodes forming a bulk gap therebetween having a bulk distance and a localized gap therebetween having a localized distance less than the bulk distance; and
    a controller configured to maintain a voltage between the electrodes that is constant during a first operating state and during a second operating state, the controller is configured to incrementally increase the voltage between the first and second electrodes above the constant voltage of the first operating state until a current detected between the electrodes is greater than a discharge threshold current.

7. The PM sensor of claim 6, wherein a breakdown voltage at which the current is detected is compared to a calculated breakdown voltage of an exhaust gas passing through the PM sensor at the localized gap;
    wherein, if the breakdown voltage is greater than the calculated breakdown voltage an installation fault flag is generated.

8. The PM sensor of claim 7, wherein the controller is configured to perform the steps of incrementally increasing the voltage and comparing the breakdown voltage to the calculated breakdown voltage multiple times at different exhaust gas temperatures;
    wherein, if the breakdown voltage is greater than the calculated breakdown voltage at least a threshold number of times of the multiple times, the installation fault flag is generated.

9. The PM sensor of claim 6, wherein the controller is configured to incrementally increase the voltage continuously or in a step-wise manner.

10. The PM sensor of claim 6, wherein the localized gap is formed by a protrusion extending from one of the first or second electrodes towards the other.

11. The PM sensor of claim 10, wherein the localized gap is formed by a protrusion extending from each of the first and second electrodes towards the other.

12. The PM sensor of claim 10, wherein the protrusion is integrally formed with the electrode from which it extends.

* * * * *